US009320530B2

(12) United States Patent
Grace

(10) Patent No.: US 9,320,530 B2
(45) Date of Patent: Apr. 26, 2016

(54) ASSISTED CUTTING BALLOON

(71) Applicant: The Spectranetics Corporation, Colorado Springs, CO (US)

(72) Inventor: Kenneth P. Grace, Woodland Park, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 156 days.

(21) Appl. No.: 13/800,214

(22) Filed: Mar. 13, 2013

(65) Prior Publication Data

US 2014/0277002 A1    Sep. 18, 2014

(51) Int. Cl.
*A61B 17/22* (2006.01)
*A61B 17/3207* (2006.01)

(52) U.S. Cl.
CPC .......... *A61B 17/22* (2013.01); *A61B 17/320725* (2013.01); *A61B 2017/22014* (2013.01); *A61B 2017/22061* (2013.01)

(58) Field of Classification Search
CPC ........... A61B 17/22; A61B 17/320725; A61B 2017/22014; A61B 2017/22061
See application file for complete search history.

(56) References Cited

U.S. PATENT DOCUMENTS

| 4,770,653 A | 9/1988 | Shturman |
| 4,785,806 A | 11/1988 | Deckelbaum |
| 4,793,359 A | 12/1988 | Sharrow |
| 4,832,023 A | 5/1989 | Murphy-Chutorian et al. |
| 4,862,886 A | 9/1989 | Clarke et al. |
| 4,878,492 A | 11/1989 | Sinofsky et al. |
| 4,966,596 A | 10/1990 | Kuntz et al. |
| 4,993,412 A | 2/1991 | Murphy-Chutorian |
| 5,010,886 A | 4/1991 | Passafaro et al. |
| 5,026,366 A | 6/1991 | Leckrone |
| 5,026,367 A | 6/1991 | Leckrone et al. |
| 5,029,588 A | 7/1991 | Yock et al. |

(Continued)

FOREIGN PATENT DOCUMENTS

| CN | 103462688 A | 12/2013 |
| DE | 2517019 A | 10/1976 |

(Continued)

OTHER PUBLICATIONS

International Search Report and Written Opinion issued in PCT/US2014/019268 on Jun. 13, 2014, 13 pages.

(Continued)

*Primary Examiner* — Katherine M Shi
*Assistant Examiner* — Michael Mendoza
(74) *Attorney, Agent, or Firm* — Faegre Baker Daniels LLP

(57) ABSTRACT

A dilation balloon is wrapped in one or more patterns with a wire or braided material having diamond abrasive or other abrasive material bonded thereto. The wire or braided material is vibrated in one or more ways to enhance the cutting action of the wire abrasive. The wire abrasive may be vibrated using high, low, or even ultrasonic waves transmitted to the wire abrasive via local or remote methods. Alternatively, the dilation balloon may be dilated with a contrast media that exhibits a high absorption to laser light. The contrast material is lased with a laser fiber or fibers inserted into the balloon interior, creating a substantial shockwave that vibrates the balloon and assists in the cracking or abrading of the surrounding plaque in contact with the dilation balloon. The cutting balloon may employ the abrasive coated wires described above or cutting blades.

14 Claims, 3 Drawing Sheets

(56) References Cited

U.S. PATENT DOCUMENTS

| | | | |
|---|---|---|---|
| 5,053,033 A | 10/1991 | Clarke | |
| 5,176,674 A | 1/1993 | Hofmann | |
| 5,192,278 A | 3/1993 | Hayes et al. | |
| 5,281,212 A | 1/1994 | Savage et al. | |
| 5,334,207 A | 8/1994 | Gay et al. | |
| 5,350,375 A | 9/1994 | Deckelbaum et al. | |
| 5,423,805 A | 6/1995 | Brucker et al. | |
| 5,468,239 A | 11/1995 | Tanner et al. | |
| 5,470,330 A | 11/1995 | Goldenberg et al. | |
| 5,514,128 A | 5/1996 | Hillsman et al. | |
| 5,722,972 A | 3/1998 | Power et al. | |
| 5,722,979 A * | 3/1998 | Kusleika | 623/1.11 |
| 5,733,301 A | 3/1998 | Forman | |
| 5,741,246 A | 4/1998 | Prescott | |
| 5,769,843 A | 6/1998 | Abela et al. | |
| 5,876,373 A | 3/1999 | Giba et al. | |
| 5,876,397 A | 3/1999 | Edelman et al. | |
| 5,944,687 A | 8/1999 | Benett et al. | |
| 6,022,309 A | 2/2000 | Celliers et al. | |
| 6,024,738 A | 2/2000 | Daikuzono et al. | |
| 6,106,515 A | 8/2000 | Winston et al. | |
| 6,167,315 A | 12/2000 | Coe et al. | |
| 6,283,958 B1 | 9/2001 | Vogl et al. | |
| 6,379,325 B1 | 4/2002 | Benett et al. | |
| 6,551,302 B1 | 4/2003 | Rosinko et al. | |
| 6,561,998 B1 | 5/2003 | Roth et al. | |
| 6,592,612 B1 | 7/2003 | Samson et al. | |
| 7,125,404 B2 | 10/2006 | Levatter | |
| 7,144,248 B2 | 12/2006 | Irwin | |
| 7,226,470 B2 | 6/2007 | Kemény et al. | |
| 7,238,178 B2 | 7/2007 | Maschke | |
| 7,572,254 B2 | 8/2009 | Hebert et al. | |
| 7,666,161 B2 | 2/2010 | Nash et al. | |
| 7,754,047 B2 | 7/2010 | Kelley | |
| 7,818,053 B2 | 10/2010 | Kassab | |
| 7,891,361 B2 | 2/2011 | Irwin | |
| 7,959,608 B2 | 6/2011 | Nash et al. | |
| 8,162,964 B2 * | 4/2012 | Piippo et al. | 606/159 |
| 8,167,810 B2 | 5/2012 | Maschke | |
| 8,454,669 B2 | 6/2013 | Irwin | |
| 8,465,452 B2 | 6/2013 | Kassab | |
| 8,551,096 B2 | 10/2013 | Perry et al. | |
| 8,574,247 B2 | 11/2013 | Adams et al. | |
| 8,684,970 B1 | 4/2014 | Koyfman et al. | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,044,619 B2 | 6/2015 | Hawkins et al. | |
| 9,072,534 B2 | 7/2015 | Adams et al. | |
| 9,138,249 B2 | 9/2015 | Adams et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 2003/0181938 A1 | 9/2003 | Roth et al. | |
| 2005/0216044 A1 | 9/2005 | Hong | |
| 2005/0251116 A1 | 11/2005 | Steinke et al. | |
| 2006/0189930 A1 | 8/2006 | Lary et al. | |
| 2006/0190022 A1 * | 8/2006 | Beyar et al. | 606/192 |
| 2006/0259005 A1 | 11/2006 | Konstantino et al. | |
| 2007/0198047 A1 | 8/2007 | Schon et al. | |
| 2008/0154293 A1 | 6/2008 | Taylor et al. | |
| 2008/0154296 A1 | 6/2008 | Taylor et al. | |
| 2009/0112239 A1 | 4/2009 | To | |
| 2009/0270846 A1 | 10/2009 | Okada et al. | |
| 2009/0270850 A1 | 10/2009 | Zhou et al. | |
| 2010/0016862 A1 | 1/2010 | Hawkins et al. | |
| 2010/0152717 A1 | 6/2010 | Keeler | |
| 2010/0222786 A1 | 9/2010 | Kassab | |
| 2011/0152683 A1 | 6/2011 | Gerrans et al. | |
| 2012/0116289 A1 | 5/2012 | Hawkins et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0046293 A1 | 2/2013 | Arai et al. | |
| 2014/0005576 A1 | 1/2014 | Adams et al. | |
| 2014/0046229 A1 | 2/2014 | Hawkins et al. | |
| 2014/0046353 A1 | 2/2014 | Adams | |
| 2014/0052114 A1 | 2/2014 | Ben-Oren et al. | |
| 2014/0052145 A1 | 2/2014 | Adams et al. | |
| 2014/0074113 A1 | 3/2014 | Hakala et al. | |
| 2014/0163592 A1 | 6/2014 | Hawkins et al. | |
| 2014/0214061 A1 | 7/2014 | Adams et al. | |
| 2014/0288570 A1 | 9/2014 | Adams | |
| 2015/0039002 A1 | 2/2015 | Hawkins | |
| 2015/0073430 A1 | 3/2015 | Hakala et al. | |
| 2015/0238208 A1 | 8/2015 | Adams et al. | |
| 2015/0238209 A1 | 8/2015 | Hawkins et al. | |
| 2015/0320432 A1 | 11/2015 | Adams | |

FOREIGN PATENT DOCUMENTS

| | | |
|---|---|---|
| DE | 1240182 C2 | 6/1994 |
| DE | 1437578 A1 | 5/1996 |
| EP | 0189329 A3 | 7/1986 |
| EP | 0355200 A1 | 2/1990 |
| EP | 1200002 B1 | 5/2002 |
| JP | H01148278 A | 6/1989 |
| KR | 100996733 B1 | 11/2010 |
| WO | 9006087 A | 6/1990 |
| WO | 9745157 A | 12/1997 |
| WO | WO0012168 A1 | 3/2000 |

OTHER PUBLICATIONS

U.S. Appl. No. 14/984,050 entitled Laser-Induced Fluid Filled Balloon Catheter, filed Dec. 30, 2015.
U.S. Appl. No. 14/984,294 entitled Electrically-Induced Fluid Filled Balloon Catheter, filed Dec. 30, 2015.
U.S. Appl. No. 14/984,308 entitled Laser-Induced Pressure Wave Emitting Catheter Sheath, filed Dec. 30, 2015.
U.S. Appl. No. 14/984,710 entitled Electrically-Induced Pressure Wave Emitting Catheter Sheath, lied Dec. 30, 2015.

* cited by examiner

ASSISTED CUTTING BALLOON

FIELD

This disclosure relates generally to cutting balloons utilized in balloon angioplasty and particularly to cutting balloons whose cutting action is assisted in one or more ways to increase the cutting action while at the same time allowing for reduced pressure within the cutting balloon.

BACKGROUND

Coronary artery disease (CAD) affects millions of Americans, making it the most common form of heart disease. CAD most often results from a condition known as atherosclerosis, wherein a waxy substance forms inside the arteries that supply blood to the heart. This substance, called plaque, is made of cholesterol, fatty compounds, calcium, and a blood-clotting material called fibrin. As the plaque builds up, the artery narrows, making it more difficult for blood to flow to the heart. As the blockage gets worse, blood flow to the heart slows, and a condition called angina pectoris, or simply angina, may develop. Angina is like a squeezing, suffocating, or burning feeling in the chest. The pain usually happens when the heart has an extra demand for blood, such as during exercise or times of emotional stress. In time, the narrowed or blocked artery can lead to a heart attack. A number of medicines can be used to relieve the angina pain that comes with CAD, but these medicines cannot clear blocked arteries. A moderate to severely narrowed coronary artery may need more aggressive treatment to reduce the risk of a heart attack.

Balloon angioplasty is a technique for mechanically widening narrowed or obstructed arteries, the latter typically being a result of atherosclerosis. An empty and collapsed balloon on a guide wire, known as a balloon catheter, is passed into the narrowed locations and then inflated to a fixed size using water pressures some 75 to 500 times normal blood pressure (6 to 20 atmospheres). The balloon is carefully inflated, first under low pressure, and then under higher pressure, until the narrowed area is widened. The balloon inflation crushes the fatty deposits it expands against, opening up the blood vessel for improved blood flow. The balloon is then deflated and withdrawn. Although the narrowing is improved in a majority of patients following balloon dilation, over time, the artery can again become narrow in as many as 15% to 20% of cases, requiring further balloon dilation. A stent may or may not be inserted at the time of balloon dilation to ensure the vessel remains open.

Percutaneous coronary intervention (PCI) is a therapeutic procedure to treat the stenotic (narrowed) coronary arteries of the heart due to CAD. These stenotic segments are caused by the buildup of plaque that forms due to atherosclerosis. PCI is usually performed by an interventional cardiologist.

PCI includes the use of balloons, stents, and atherectomy devices. PCI is accomplished with a small balloon catheter inserted into an artery in the groin or arm, and advanced to the narrowing in the coronary artery. The balloon is then inflated to enlarge the narrowing in the artery. When successful, PCI allows more blood and oxygen to be delivered to the heart muscle and can relieve the chest pain of angina, improve the prognosis of individuals with unstable angina, and minimize or stop a heart attack without having the patient undergo open heart coronary artery bypass graft (CABG) surgery.

Balloon angioplasty is also called percutaneous transluminal coronary angioplasty (PTCA). Both PCI and PTCA are non-surgical procedures. Balloon angioplasty can also be used to open narrowed vessels in many other parts of the body.

Peripheral angioplasty (PA) refers to the use of a balloon to open a blood vessel outside the coronary arteries. It is commonly done to treat atherosclerotic narrowing of the abdomen, leg, and renal arteries. PA can also be done to treat narrowing in veins. Often, PA is used in conjunction with peripheral stenting and atherectomy. For example, doctors can perform carotid angioplasty to open narrowed carotid arteries, which are the arteries that supply blood to the brain. A stroke most often occurs when the carotid arteries become blocked and the brain does not get enough oxygen. Balloon angioplasty can also be performed in the aorta (the main artery that comes from the heart), the iliac artery (in the hip), the femoral artery (in the thigh), the popliteal artery (behind the knee), and the tibial and peroneal arteries (in the lower leg). The use of fluoroscopy assists the doctor in the location of blockages in the coronary arteries as the contrast dye moves through the arteries. A small sample of heart tissue (biopsy) may be obtained during the procedure to be examined later under the microscope for abnormalities.

A cutting balloon (CB) is an angioplasty device used in PCI and PTCA and is a proven tool for the mechanical challenges of complex lesions that are often resistant to conventional balloon angioplasty. A CB has a special balloon with small blades that are activated when the balloon is inflated. The CB typically has three or four atherotomes (microsurgical blades) bonded longitudinally to its surface, suitable for creating discrete longitudinal incisions in the atherosclerotic target coronary segment during balloon inflation. Cutting balloon angioplasty (CBA) features three or four atherotomes, which are 3-5 times sharper than conventional surgical blades. The atherotomes, which are fixed longitudinally on the outer surface of a non-complaint balloon, expand radially and deliver longitudinal incisions in the plaque or target lesion, relieving its hoop stress. With the CBA, the increase in the vessel lumen diameter is obtained in a more controlled fashion and with a lower balloon inflation pressure than PCI and PTCA procedures utilizing conventional balloons. This controlled dilation could reduce the extent of vessel wall injury and the incidence of restenosis.

The advantage of CBA is its ability to reduce vessel stretch and vessel injury by scoring the target coronary segment longitudinally rather than causing an uncontrolled disruption of the atherosclerotic plaque or target lesion. The atherotomes deliver a controlled fault line during dilation to ensure that the crack propagation ensues in an orderly fashion. The CB also dilates the target vessel with less force to decrease the risk of a neoproliferative response and restenosis. The unique design of the CB is engineered to protect the vessel from the edges of the atherotomes when it is deflated. This minimizes the risk of trauma to the vessel as the balloon is passed to and from the target coronary segment. With CBA, balloon inflation pressures can still range between 14-16 atmospheres, though lower inflation pressures are recommended.

Angioplasty balloons that employ a woven mesh, cutting strings, or wires are also known in the art. These balloons have been shown to be more flexible and safer than balloons employing cutting blades and edges. The scoring elements can, for example, be in the form of a single wire or a plurality of wires wrapped around a dilation balloon in a helical configuration. Other angioplasty cutting balloon catheter assemblies have a catheter equipped with an inflatable balloon with an interior cavity and an expandable covering around the balloon. The expandable covering may be in the form of a mesh coating having a cross-hatched pattern. The mesh coating may be made of plastic or metal fibers, where at least some of the fibers have cutting edges. In operation, the cutting edges abrade the stenosis, plaque, or lesions along the vessel walls when the catheter assembly is reciprocally moved longitudinally or rotationally after inflation of the balloon.

SUMMARY

These and other needs are addressed by the various aspects, embodiments, and configurations of the present disclosure. The disclosure is generally directed to the use of vibrations to enhance the performance of cutting balloons, particularly in angioplasty, in treating lesions, occlusions and plaque.

A method, according to this disclosure, can perform balloon angioplasty by the steps of:

(a) inserting an assisted cutting balloon into a target coronary segment partially occluded with plaque, the assisted cutting balloon having one or more cutting devices positioned on an exterior of the dilation balloon; and (b) inflating the dilation balloon and vibrating the one or more cutting devices while the cutting balloon is inserted into the target coronary segment.

The expanding and vibrating dilation balloon can crush softer portions of the plaque, and/or the vibrating wire abrasive can cut the harder or calcified portions of the plaque.

An assisted cutting balloon for performing balloon angioplasty, according to this disclosure, can include:

(a) a dilation balloon;

(b) one or more cutting devices operably positioned on an exterior of the dilation balloon;

(c) a laser light source terminating at a distal end in the interior of the dilation balloon; and (d) a contrast medium for inflating the dilation balloon.

As the dilation balloon is inflated with the contrast medium and/or after inflation, the laser light source can transmit pulsed laser light into the contrast medium creating shockwaves that propagate through the contrast medium, thereby causing the cutting device(s) to vibrate and assist in the cracking or abrading of the surrounding plaque in contact with the balloon.

The contrast material commonly exhibits a high degree of optical absorption to the laser light. When a laser fiber or fibers inserted into the balloon interior emit optical energy into the contrast material, the material is believed to experience a rapid rate of energy absorption, creating the shockwave.

An assisted cutting balloon for performing balloon angioplasty, according to this disclosure, can include:

(a) a dilation balloon;

(b) one or more cutting devices operably positioned on an exterior of the dilation balloon; and (c) a flexible wire waveguide connected at a distal end to the cutting device(s) and at a proximal end to an ultrasonic apparatus.

The ultrasonic apparatus can transmit ultrasonic waves through the flexible wire waveguide to the cutting device(s) causing the cutting device(s) to vibrate as and/or after the dilation balloon is inflated, thereby assisting in the cracking or abrading of the surrounding plaque in contact with the balloon.

The cutting device(s) can be a wire abrasive bound to an exterior of the dilation balloon.

In one application, wire or braid material is constructed with a diamond abrasive or other types of abrasive cutting material and is wrapped around a dilation balloon in a helical or other type of configuration. The wire or braided material is vibrated using high, low, or even ultrasonic waves transmitted to the wire or braided material via local or remote methods, substantially enhancing the ability to cut or abrade the plaque.

The guide wire can be inserted into a vasculature system and moved past the target coronary segment, and the assisted cutting balloon translated over the guide wire to the target coronary segment.

In one procedure, the dilation balloon can be inflated with a contrast medium. Specifically, a laser fiber and the assisted cutting balloon are translated along over the guide wire to the target coronary segment, with the distal end of the laser fiber terminating in the middle of the dilation balloon. A laser generator connected to a proximal end of the laser fiber emits laser light from the distal end of the laser fiber at a very short pulse duration, thereby creating shockwaves that propagate through the contrast medium as the dilation balloon is inflating, causing the cutting device(s) to vibrate. The vibrations cause the cutting device(s) to cut or abrade harder or calcified portions of the plaque as the dilation balloon is inflating. The laser generator typically generates 308 nm laser light at pulse durations ranging from 120-140 nsec. While other types of laser generators can be employed, a common laser generator is an excimer laser.

To assist positioning within the body, the assisted cutting balloon, guide wire, and laser fiber can be enclosed in a multi-lumen catheter.

In another procedure, an ultrasonic apparatus having a flexible wire waveguide connected at a proximal end to the ultrasonic apparatus and connected at a distal end to the cutting device(s) transmits ultrasonic waves through the flexible wire waveguide to the cutting device(s), causing the cutting device(s) to vibrate. The vibrating cutting device(s) cut the harder or calcified portions of the plaque as and/or after the dilation balloon is inflated.

In any of the above procedures, the balloon is commonly inflated to pressures ranging between about 1-30 atmospheres, 5-25 atmospheres, and 10-20 atmospheres.

The present disclosure can provide benefits relative to conventional cutting balloons. The use of vibration, at low, medium, or high frequencies, can enhance dramatically the performance of cutting balloons. Cutting device(s), particularly the wire or braid materials constructed with diamond abrasives or other type of abrasive cutting materials, can cut, abrade, or otherwise modify plaque, particularly calcified or hard plaque, while leaving surrounding soft tissue and compliant balloon material substantially unaltered and undamaged. This can be a very effective method to assist in cracking or modifying plaque in arteries. The disclosure can avoid the need to inflate balloons to very high pressures (e.g., from about 15 to about 30 atms), thereby permitting the use of lower pressures (e.g., typically no more than about 10 atms and even more typically no more than about 7.5 atms).

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_m$, $Y_1$-$Y_n$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_3$).

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

"Contrast medium" or "contrast media" is generally any substance used to change the imaging characteristics of a patient, thereby providing additional information such as anatomical, morphological, and/or physiological. Contrast media can, for example, provide information regarding vasculature, vascular integrity, and/or qualitative assessment of vasculature function or operation. Positive contrast agents increase the attenuation of tissue, blood, urine, or outline spaces such as the gastrointestinal lumen or subarachnoid space. Two primary types of positive contrast agents are barium sulfate agents and various halogenated (e.g., iodated) compounds. Negative contrast agents normally decrease attenuation by occupying a space, such as the bladder, gastrointestinal tract, or blood vessels. Negative contrast agents are typically gases, such as carbon dioxide and nitrous oxide. Another type of contrast media, namely MRI contrast agents, uses typically superparamegnetism. Finally, ultrasound contrast media, namely sonagraphic contrast agents, are typically composed of gas bubbles (air or perfluor gases) stabilized by a shell of phospholipids, surfactants, albumin, or polymers.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof, shall include all those described in the summary of the invention, brief description of the drawings, detailed description, abstract, and claims themselves.

"Ultrasound" refers to sound or other vibrations having an ultrasonic frequency, which is commonly a frequency above about 20 thousand cycles per second (20,000 Hz).

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible, utilizing alone or in combination, one or more of the features set forth above or described in detail below.

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
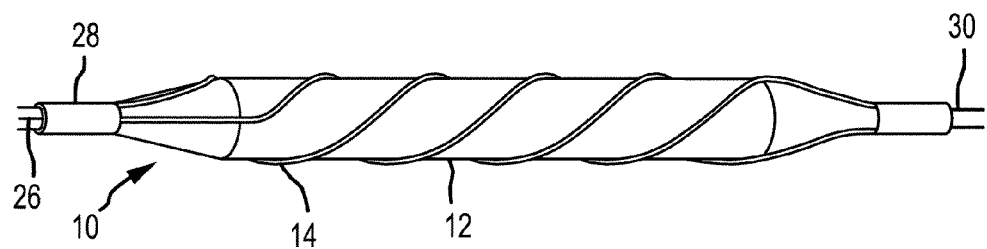
FIG. 1 shows a schematic illustration of an embodiment of an assisted cutting balloon.

FIG. 1 shows a schematic illustration of an embodiment of an assisted cutting balloon. Referring now to FIG. 1, Assisted Cutting Balloon 10 includes a Dilation Balloon 12, which may be any conventional angioplasty balloon such as commonly used by interventional cardiologists or radiologists, and a Wire Abrasive 14 mounted, attached, affixed, or otherwise bound, in a helical configuration, to the exterior of Dilation Balloon 12. Wire Abrasive 14 may be one wire strand or many wire strands wrapped or braided together. The wire may be composed of any suitable material, with one or more metal and/or plastic fibers being typical. Diamond material or any other suitable abrasives may be used as an abrasive bonded to the wire. Diamond wire impregnated with diamond dust is relatively inexpensive and is readily available in various diameters and lengths. Multiple configurations of Dilation Balloon 12 may be used with different types of cutting wire or string wrap patterns or braids, such as diamond, cross-hatch, woven or unwoven mesh, reverse helical, longitudinal, radial, etc., around the exterior of the Dilation Balloon 12 and with different types of abrasive coated wire or cutting blades or atherotomes in a variety of geometrical shapes bonded or applied to Dilation Balloon 12. Other cutting balloon configurations known to those of skill in the art may be employed as the Dilation Balloon 12. Guide Wire 30 is inserted into the vasculature system of the subject and past Target Coronary Segment 32 (see FIG. 3). Assisted Cutting Balloon 10 is translated over Guide Wire 30 to Target Coronary Segment 32.

Figure 2:
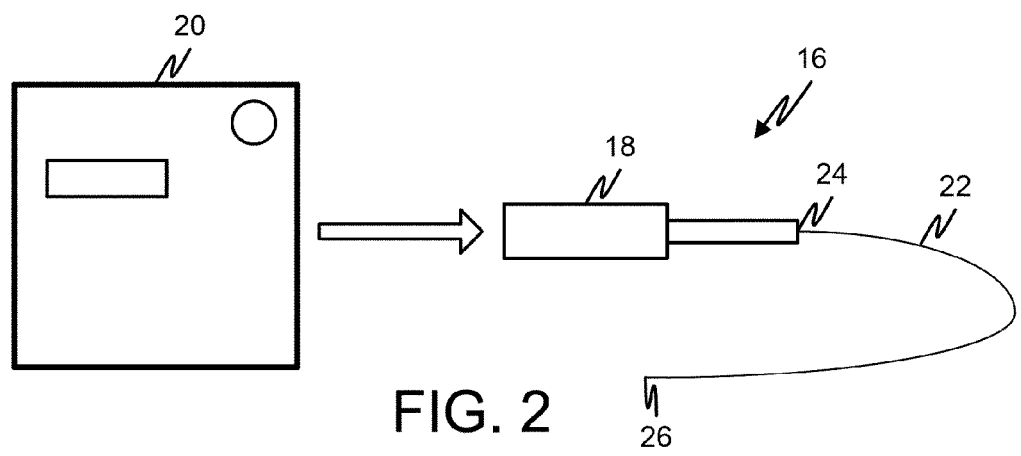
FIG. 2 shows a schematic diagram of an embodiment of an ultrasonic generator apparatus.

FIG. 2 shows a schematic diagram of an embodiment of an ultrasonic generator apparatus. Referring now to FIG. 2, Ultrasonic Apparatus 16 includes a Piezoelectric Converter And Acoustic Horn 18 that operates with a resonant frequency. Piezoelectric Converter And Acoustic Horn 18 is driven by Ultrasonic Generator 20 at an adjustable resonant frequency or set of plural frequencies. The frequencies can be temporally fixed or varied during Assisted Cutting Balloon 12 operation. This ensures that resonance of Piezoelectric Converter And Acoustic Horn 18 is achieved despite minor alterations in the resonant frequency of the system. In addition, Ultrasonic Generator 20 has adjustable input power dial settings.

Flexible Wire Waveguide 22 is connected to Piezoelectric Converter And Acoustic Horn 18 at a Proximal End 24 and fixed tightly into the radiating face of Piezoelectric Converter And Acoustic Horn 18 ensuring a rigid connection between the two. Distal End 26 of Flexible Wire Waveguide 22 is rigidly connected to a Proximal End 28 of Wire Abrasive 14 (see FIG. 1). Other local or remote methods may be used to transmit high, low, or ultrasonic waves to Flexible Wire Waveguide 22 such as.

Figure 3:
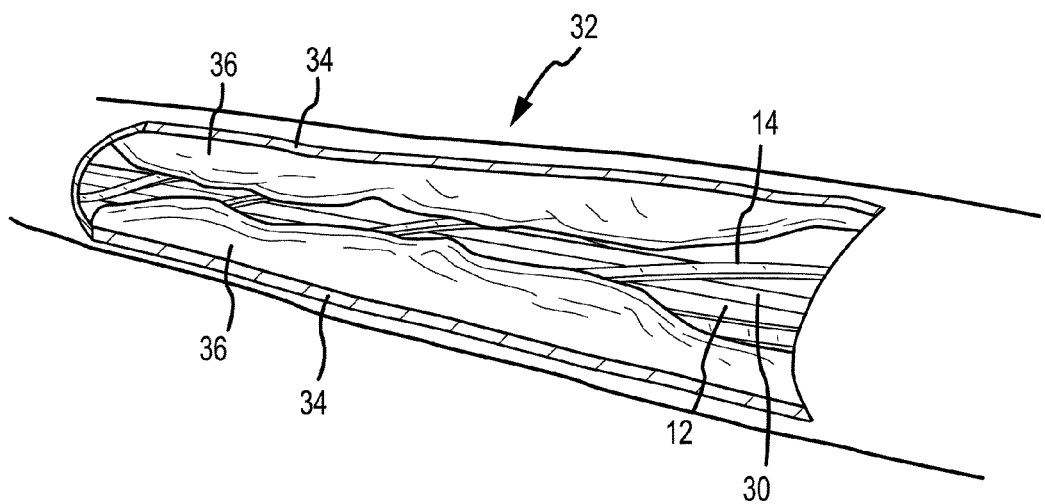
FIG. 3 shows a partial cross section view of a partially occluded artery with an assisted cutting balloon in place prior to inflation.

FIG. 3 shows a partial cross section view of a partially occluded artery with an assisted cutting balloon in place prior to inflation. Referring now to FIG. 3, Assisted Cutting Balloon 10 has been translated over Guide Wire 30 to Target Coronary Segment 32. The interior of Artery 34 is partially occluded with deposits of Plaque 36.

Figure 4:
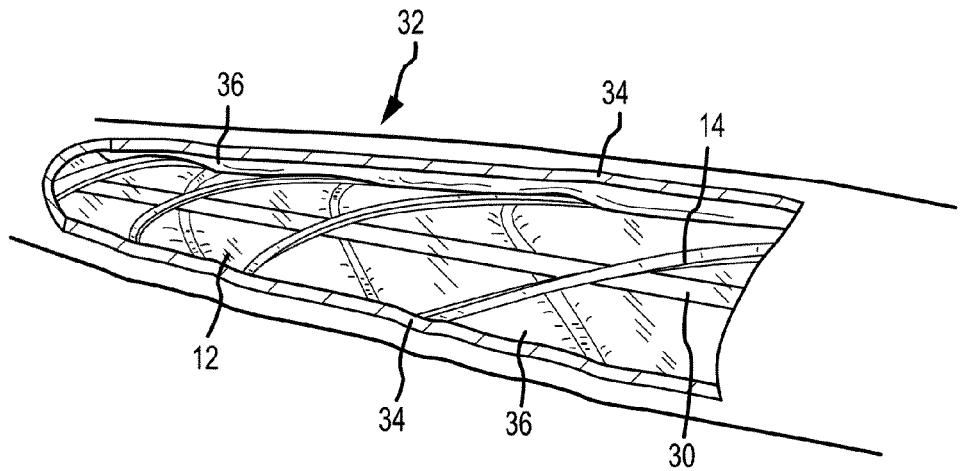
FIG. 4 shows a partial cross section view of a partially occluded artery with an assisted cutting balloon in place and inflated.

FIG. 4 shows a partial cross section view of a partially occluded artery with an assisted cutting balloon in place and inflated. Referring now to FIG. 4, as Dilation Balloon 12 is inflated, Ultrasonic Apparatus 16 is powered on. Flexible Wire Waveguide 22 causes Wire Abrasive 14 to vibrate. Thus, as Wire Abrasive 14 of Dilation Balloon 12 comes into contact with Plaque 36, Dilation Balloon 12 crushes the softer portions of Plaque 36 and the cutting action of Wire Abrasive 14, which is enhanced due to the vibration imparted via Flexible Wire Waveguide 22, cuts the harder or calcified portions of Plaque 36. The enhanced cutting action reduces the inflation pressure necessary to 5 to 10 atmospheres which reduces the chance for damage to Artery 34.

Figure 5:
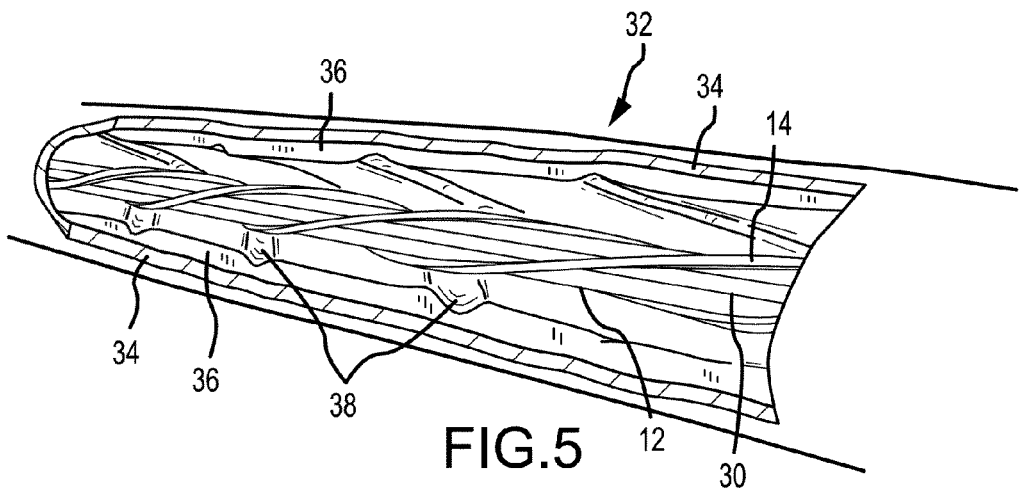
FIG. 5 shows a partial cross section view of a partially occluded artery with an assisted cutting balloon after deflation and ready for removal.

FIG. 5 shows a partial cross section view of a partially occluded artery with an assisted cutting balloon after deflation and ready for removal. Referring now to FIG. 5, Striations 38 can be seen in crushed Plaque 36 due to the cutting action of Wire Abrasive 14. Assisted Cutting Balloon 10 is now ready for removal over Guide Wire 30.

Figure 6:
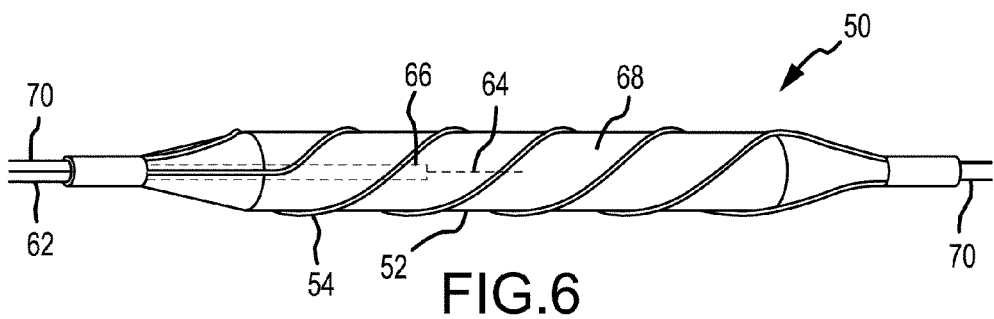
FIG. 6 shows a schematic illustration of another embodiment of an assisted cutting balloon.

FIG. 6 shows a schematic illustration of another embodiment of an assisted cutting balloon. Referring now to FIG. 6, Assisted Cutting Balloon 50 includes a Dilation Balloon 52, which may be any conventional angioplasty balloon such as commonly used by interventional cardiologists or radiologists, and a Wire Abrasive 54 mounted over or attached to Dilation Balloon 52. Wire Abrasive 54 may be one wire strand or many wire strands braided together. Diamond material or any other suitable abrasives may be used as an abrasive bonded to the wire. Diamond wire impregnated with diamond dust is relatively inexpensive and is readily available in various diameters and lengths. Multiple configurations of Dilation Balloon 52 may be used with different types of wire wrap patterns or braids, such as diamond or cross-hatch, helical, etc., and with different types of abrasive coated wire or cutting blades in a variety of geometrical shapes bonded or applied to Dilation Balloon 12. Guide Wire 70 is inserted into the subject and Assisted Cutting Balloon 50 is translated over Guide Wire 70 to a target coronary segment, such as Target Coronary Segment 32 shown in FIG. 3.

Figure 7:
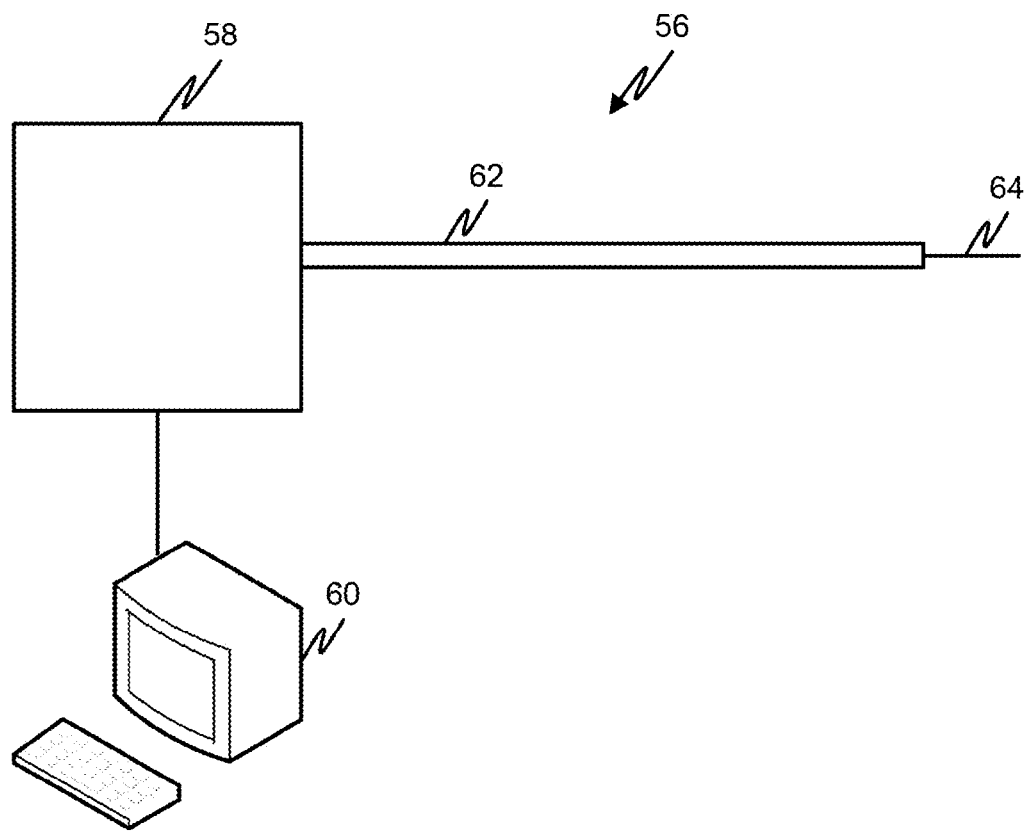
FIG. 7 shows a schematic diagram of an embodiment of a laser generator apparatus.

FIG. 7 shows a schematic diagram of an embodiment of a laser generator apparatus. Referring now to FIG. 7, a laser light source such as Laser Apparatus 56 includes a Laser Generator 58 controlled by a Computer 60. Flexible Cladding 62 shields Laser Fiber 64, which may be a single fiber or multiple fibers. Flexible Cladding 62 runs parallel with Guide Wire 70 and both may be enclosed in a multi-lumen catheter along with Assisted Cutting Balloon 10. Distal End 66 (see FIG. 6) of Flexible Cladding 62 terminates in the middle of Dilation Balloon 52. Laser Fiber 64 extends a short distance from Distal End 66. When Assisted Cutting Balloon 50 has been translated over Guide Wire 70 to a target coronary segment, it will appear like that shown in FIG. 3, where the interior of Artery 34 of Target Coronary Segment 32 is partially occluded with deposits of Plaque 36.

Substituting now Assisted Cutting Balloon 50 for Assisted Cutting Balloon 10 shown in FIG. 4, Dilation Balloon 52 is inflated with Contrast Medium 68. Contrast Medium 68 may be one of many different compounds as found in the ACR Manual of Contrast Media, Version 8, 2012. As Dilation Balloon 52 is inflated, Laser Apparatus 56 is activated, which, in one embodiment, may be an excimer laser that emits 308 nm laser light at very short pulse durations (120-140 nsec.) from Laser Fiber 64. Contrast Medium 68 exhibits a very high absorption to this laser light. Due to the high absorption and short pulse width of the laser light, shockwaves are created that propagate through the volume of Contrast Medium 68 within Dilation Balloon 52. The shockwaves assist in the cracking, crushing, or modification of Plaque 36 by Dilation Balloon 52. The shockwave also causes Wire Abrasive 54 to vibrate. Thus, as Wire Abrasive 54 of Dilation Balloon 52 comes into contact with Plaque 36, Dilation Balloon 52, assisted by the shockwaves as well as by inflation, crushes the softer portions of Plaque 36, and the cutting action of Wire Abrasive 54, which is enhanced due to the vibration imparted via the shockwaves traveling through the volume of Contrast Medium 68, cuts the harder or calcified portions of Plaque 36. Dilation Balloon 52 is then deflated and ready for removal as shown in FIG. 5. Striations 38 will also be seen in crushed Plaque 36 due to the cutting action of Wire Abrasive 54.

A number of variations and modifications of the disclosure can be used. It would be possible to provide for some features of the disclosure without providing others.

For example in one alternative embodiment, cutting blades may be used instead of abrasive wire.

In another example, other Assisted Cutting Balloon 12 vibrating mechanisms may be employed. Examples include mechanically induced vibration (e.g., by a micro-vibration motor), electrically induced vibration, electromechanically induced vibration (e.g., by a micro-electromechanical system), magnetically induced vibration, electromagnetically induced vibration, and vibration induced by other sound or acoustical frequencies.

In another example, the vibration source may be positioned either remotely, as discussed and shown above, or locally, such as in the proximity of the balloon itself, or a combination thereof. Micro-components can be positioned in or near the balloon in the catheter itself whereby attenuation of vibrations remotely generated is reduced. For example, a micro-vibration motor, micro-electromechanical system, or micro-piezoelectric transducer can be positioned in the catheter in proximity to the balloon.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. For example, in the foregoing Detailed Description, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included descriptions of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for performing balloon angioplasty, the method comprising the steps of:
   (a) inserting an assisted cutting balloon into a target coronary segment partially occluded with plaque, the assisted cutting balloon having a dilation balloon with one or more cutting devices operably positioned on an exterior of the dilation balloon and a laser fiber within the dilation balloon;
   (b) inflating the dilation balloon with a liquid medium; and
   (c) vibrating the one or more cutting devices by emitting laser light from the laser fiber, thereby creating shockwaves that propagate through the liquid medium and causing the one or more cutting devices to vibrate, wherein the laser light is 308 nm laser light pulsed at durations ranging from 120-140 nsec; and
   whereby the inflating and/or inflated dilation balloon crushes softer portions of the plaque and the vibrating one or more cutting devices cuts relative harder or calcified portions of the plaque.

2. The method according to claim 1, wherein the one or more cutting devices comprise one or more wire abrasives bound to the exterior of the dilation balloon and wherein step (a) further comprises the steps of:
   inserting a guide wire into a vasculature system and past the target coronary segment; and
   translating the assisted cutting balloon over the guide wire to the target coronary segment.

3. The method according to claim 2, wherein the liquid medium includes a contrast medium.

4. The method according to claim 3, further comprising the steps of:
   translating the laser fiber along with the assisted cutting balloon over the guide wire to the target coronary segment, the distal end of the laser fiber terminating in the middle of the dilation balloon.

5. The method according to claim 4, wherein the translating step further comprises the step of:
   enclosing the assisted cutting balloon, the guide wire, and the laser fiber into a multi-lumen catheter.

6. The method according to claim 4, wherein the
   the laser light is emitted from the distal end of the laser fiber, and wherein the laser light is generated from an excimer laser.

7. The method according to claim 4, further comprising the step of:
   assisting the crushing of the softer portions of the plaque by the shockwaves propagating within the dilation balloon.

8. The method according to claim 1, wherein step (b) further comprises the step of:
   inflating the dilation balloon to a pressure ranging between 5 to 10 atmospheres.

9. An assisted cutting balloon for performing balloon angioplasty comprising:
   a dilation balloon;
   one or more cutting devices operably positioned on an exterior of the dilation balloon;
   a laser light source terminating at a distal end in the interior of the dilation balloon, wherein laser light generated by the laser light source is 308 nm laser light pulsed at durations ranging from 120-140 nsec; and
   a contrast medium for inflating the dilation balloon;
   whereby, as and/or after the dilation balloon is inflated with the contrast medium, the laser light source transmits pulsed laser light into the contrast medium creating shockwaves that propagate through the contrast medium causing the one or more cutting devices to vibrate.

10. The assisted cutting balloon for performing balloon angioplasty according to claim 9, wherein the one or more cutting devices comprise a wire abrasive bound to the exterior of the dilation balloon and further comprising:
    a guide wire for translating the assisted cutting balloon and the laser light source to a target coronary segment partially occluded with plaque, wherein the guide wire is inserted into a vasculature system and past the target coronary segment.

11. The assisted cutting balloon for performing balloon angioplasty according to claim 9, wherein the laser light source further comprises:
    a laser fiber translated along with the assisted cutting balloon to the target coronary segment;
    a laser generator connected to a proximal end of the laser fiber and the distal end of the laser fiber terminates in the middle of the dilation balloon; and
    a laser light emitted from the distal end of the laser fiber at very short pulse durations creating shockwaves that propagate through the contrast medium as the dilation balloon is inflating, causing the one or more cutting devices to vibrate, wherein, as the dilation balloon is inflated, the one or more cutting devices vibrate and cut harder or calcified portions of the plaque.

12. The assisted cutting balloon for performing balloon angioplasty according to claim 11, further comprising:
    a multi-lumen catheter for enclosing the assisted cutting balloon, the guide wire, and the laser fiber.

13. The assisted cutting balloon for performing balloon angioplasty according to claim 9, wherein a proximal end of the laser light source is coupled to an excimer laser generator.

14. The assisted cutting balloon for performing balloon angioplasty according to claim 10, wherein the wire abrasive is diamond dust, and the wire wrap pattern of the wire abrasive bound to the dilation balloon is one or more of diamond, cross-hatch, mesh, longitudinal, radial, and helical.

* * * * *